United States Patent
Inukai et al.

(10) Patent No.: US 11,911,052 B2
(45) Date of Patent: Feb. 27, 2024

(54) TREATMENT METHOD

(71) Applicant: TERUMO KABUSHIKI KAISHA, Shibuya (JP)

(72) Inventors: Takito Inukai, Fujinomiya (JP); Tetsuya Fukuoka, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 234 days.

(21) Appl. No.: 16/832,633

(22) Filed: Mar. 27, 2020

(65) Prior Publication Data
US 2020/0305899 A1 Oct. 1, 2020

(30) Foreign Application Priority Data
Mar. 29, 2019 (JP) ................. 2019-065408

(51) Int. Cl.
*A61B 17/22* (2006.01)

(52) U.S. Cl.
CPC .... *A61B 17/22* (2013.01); *A61B 2017/22001* (2013.01); *A61B 2017/22038* (2013.01); *A61B 2017/22079* (2013.01)

(58) Field of Classification Search
CPC ................ A61B 17/22; A61B 17/3207; A61B 2017/22001; A61B 2017/22038; A61B 2017/22051; A61B 2017/22079
See application file for complete search history.

(56) References Cited

U.S. PATENT DOCUMENTS

2014/0358123 A1* 12/2014 Ueda ................. A61M 25/0053
604/510
2018/0064526 A1* 3/2018 Walzman ................. A61B 8/12

OTHER PUBLICATIONS

Chou Shing-Hsien, et al., "Double Guiding Catheters for Complex Percutaneous Coronary" Texas Heart Institute Journal, 2012 (month unknown); 39(1): 112-115, 6 pages.

* cited by examiner

*Primary Examiner* — Darwin P Erezo
*Assistant Examiner* — Christian D Knauss
(74) *Attorney, Agent, or Firm* — BUCHANAN INGERSOLL & ROONEY PC

(57) ABSTRACT

A treatment method reduces the time required to exchange a long catheter which is introduced from an arm to treat the lower limb artery. The treatment method involves introducing a first catheter from an artery of one arm of the patient to dispose a distal portion of the first catheter at least in front of the lesion area in the lower limb artery; introducing a second catheter from an artery of the other arm of the patient; disposing a first treatment catheter in the lesion area through the first catheter; treating the lesion area with the first treatment catheter; and assisting the treatment with the second catheter and/or a second treatment catheter that is inserted into the second catheter.

17 Claims, 2 Drawing Sheets

TREATMENT METHOD

CROSS-REFERENCES TO RELATED APPLICATIONS

This application is based on and claims priority to Japanese Patent Application No. 2019-065408 filed on Mar. 29, 2019, the entire content of which is incorporated herein by reference.

FIELD OF THE INVENTION

The present invention generally relates to a treatment method for a lesion area in which catheters are introduced from the radial arteries of both arms to treat the lesion area in a lower limb artery.

BACKGROUND DISCUSSION

In recent years, in order to treat a lower limb artery (an artery in a lower limb of a living body), a technique (transradial intervention: TRI) of introducing a catheter from an artery of an arm, particularly from a radial artery to perform a treatment is performed for reasons such as reducing physical burden on a patient and early patient discharge. An example of this technique is disclosed in U.S. Patent Application Publication No. 2014/0358123.

SUMMARY OF THE INVENTION

When the catheter is inserted from a blood vessel of the arm to treat a lesion area in a blood vessel of the lower limb, the inner surface of the blood vessel before and after treatment may be confirmed using image diagnosis to assist the treatment. For example, when an intravascular ultrasound (IVUS) imaging catheter is used as a diagnostic catheter, a treatment catheter such as a balloon catheter is removed for the moment and exchanged with the diagnostic catheter, and the diagnostic catheter is inserted into the blood vessel.

When only one guiding catheter or a catheter assembly including one set of an outer guiding catheter and an inner catheter is used, it may take the time to exchange the diagnostic catheter with the treatment catheter, and the catheter may come into contact with an insanitary field or kink, so that the catheter is required to be exchanged with a new catheter.

Alternatively, when the catheter moves in the aorta, emboli separated from the inner wall of the aorta may scatter to the renal artery or the superior mesenteric artery to cause ischemia.

For example, in a high emergency case such as when there is a possibility of intestinal necrosis occurring due to the advancement of ischemia caused by acute superior mesenteric artery occlusion (SMAO), the catheter disposed in a lesion area may be removed to interrupt the treatment.

Texas Heart Institute Journal 2012; 39 (1): 112-115 discloses a method for simultaneously treating a main branch and a bifurcated branch of a bifurcated blood vessel of a coronary artery from the right and left radial arteries. However, the foregoing journal does not disclose how to treat a lesion area in one blood vessel which takes time to treat due to the absence of bifurcated branches and a long length of the lesion area as in a superficial femoral artery of lower limb arteries or due to the advancement of calcification.

It is important to shorten the procedure time for a difficult-to-treat lesion area and efficiently use the guiding catheter or the treatment catheter from the viewpoint that the burden on the patient is reduced and the procedure time is shortened to improve the medical economic efficiency.

(1) According to one aspect, there is provided a treatment method for a patient having a lesion area in a lower limb artery. The treatment method includes introducing a first catheter from an artery of one arm of the patient to dispose a distal portion of the first catheter at least in front of the lesion area in the lower limb artery; introducing a second catheter from an artery of the other arm of the patient; a second disposition step of disposing a first treatment catheter in the lesion area through the first catheter; treating the lesion area with the first treatment catheter; and assisting the treatment with the second catheter and/or a second treatment catheter that is inserted into the second catheter.

(2) In the treatment method described in (1), at least one of the artery of the one arm and the artery of the other arm may be a conventional radial artery.

(3) In the treatment method described in (1), at least one of the artery of the one arm and the artery of the other arm may be a distal radial artery or a radial artery in a snuffbox.

Since one catheter is inserted from each of both arms into a lesion area in a lower limb artery which it takes the time to treat, the time required to exchange a treatment catheter or a diagnostic catheter is reduced, and there is no interruption in the treatment of the lesion area even when acute embolism occurs in a site other than the lesion area; and thereby, it is possible to complete the entire treatment of a patient in a short period of time.

A treatment method according to another aspect involves treating a patient having a lesion area in a lower limb artery of a body of the patient who has a first arm and a second arm. The treatment method comprises: introducing a first catheter into an artery of the first arm of the patient; advancing the first catheter, which has been introduced into the artery of the first arm of the patient, in the body of the patient to position a distal portion of the first catheter adjacent the lesion area in the lower limb artery; introducing a second catheter into an artery of the second arm of the patient; and advancing the second catheter, which has been introduced into the artery of the second arm of the patient, in the body of the patient to position a distal portion of the second catheter adjacent the lesion area in the lower limb artery. The method further involves introducing a treatment catheter into a lumen in the first catheter or into a lumen in the second catheter and advancing the treatment catheter along the lumen to position a distal end portion of the treatment catheter outside and distally beyond the lumen; treating the lesion area by creating a hole in the lesion area or enlarging a hole in the lesion area through operation of the first treatment catheter that is positioned outside the lumen, with the treating of the lesion area producing emboli or cholesterol crystals; and the treating of the lesion area being carried out after the advancing of the first catheter to the position adjacent the lesion area and after the advancing of the second catheter to the position adjacent the lesion area; and creating suction in the lumen of the first catheter or in the lumen of the second catheter to draw the emboli or the cholesterol crystals into the lumen of the first catheter or into the lumen of the second catheter.

DETAILED DESCRIPTION

Figure 1:
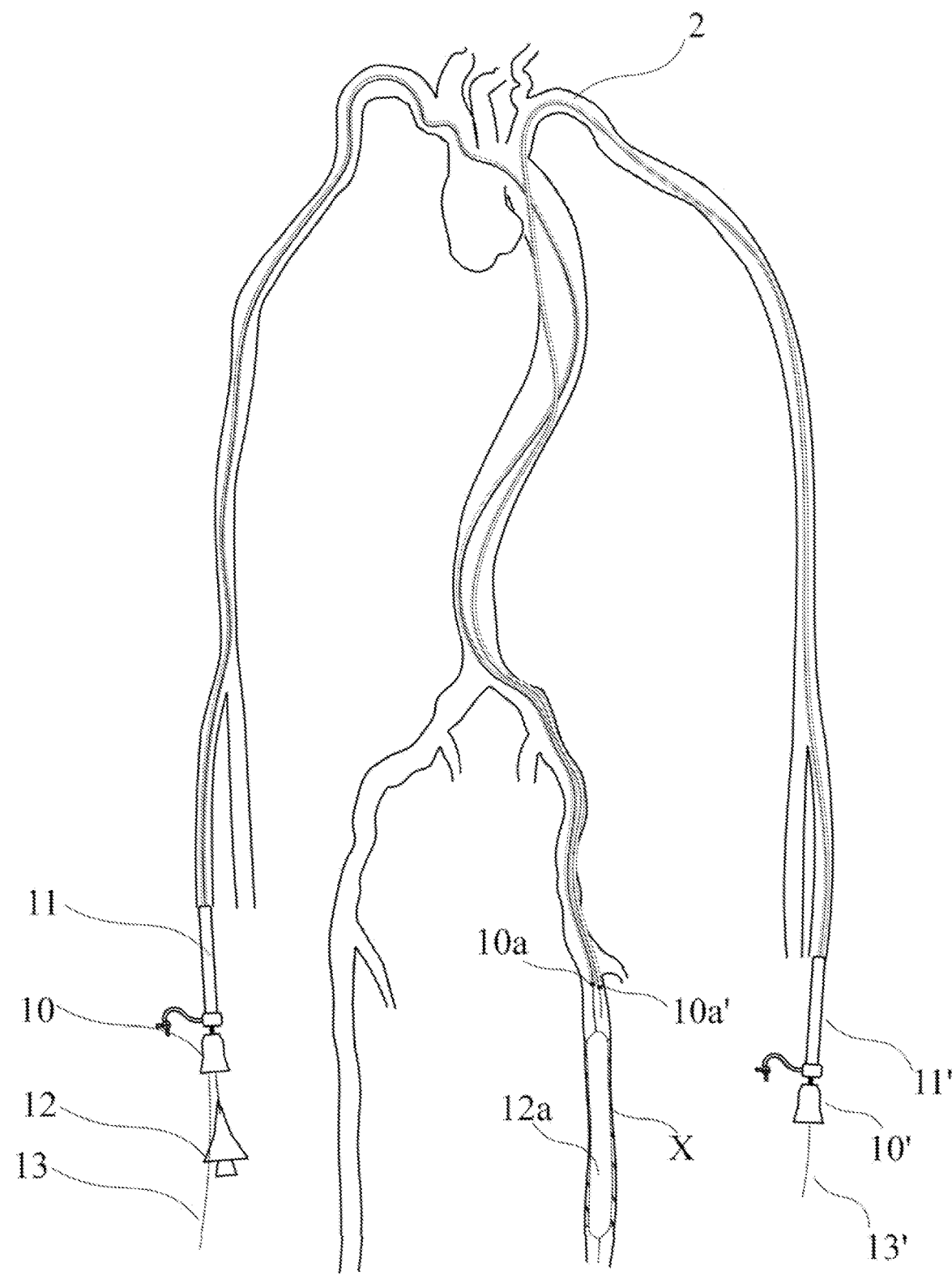
FIG. 1 is an overall view illustrating a treatment method and the like according to an embodiment.
Figure 2:
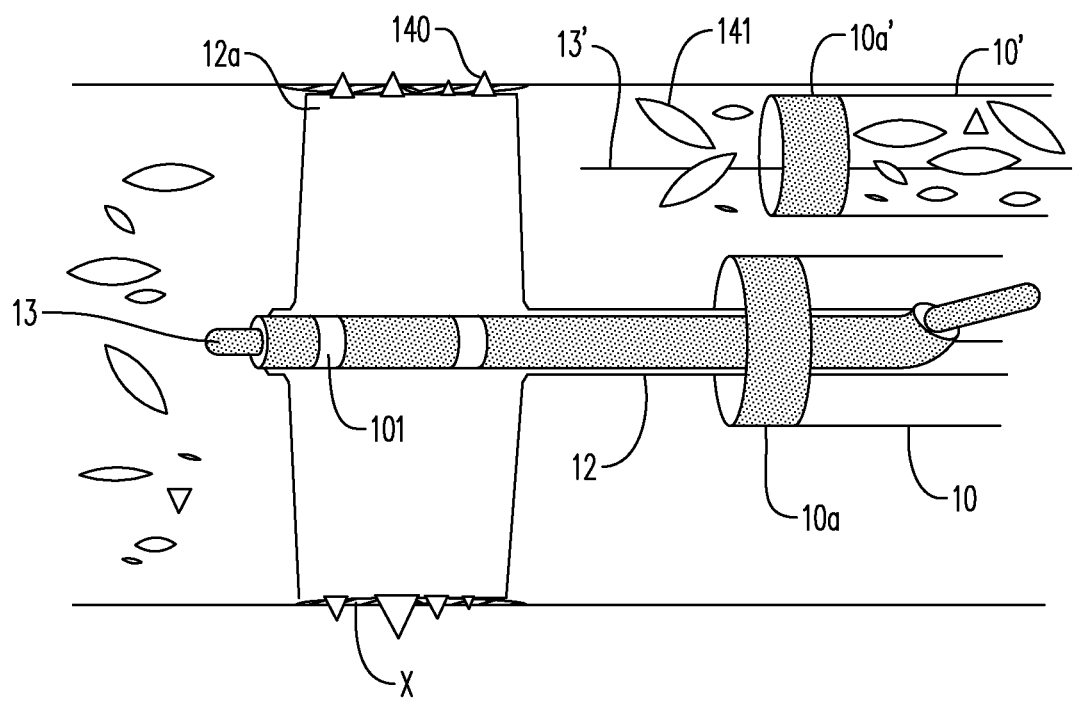
FIG. 2 is an enlarged schematic cross-sectional view illustrating a treatment step of treating a lesion area using a first treatment catheter and an assistance step of assisting a treatment by aspirating and removing scattered plaque and the like using a second catheter.

Set forth below with reference to the accompanying drawings is a detailed description of embodiments of a treatment method for treating a lesion area representing examples of the inventive treatment method disclosed here. The dimensions or scales on the drawings may be exaggerated or different from actuality/reality for convenience of description and illustration. In addition, in the following description, a hand-side of a catheter is referred to as a "proximal end", and a side of the catheter which is inserted into a living body is referred to as a "distal end".

In this specification, the term "treatment" implies dilating a stenosed site or an occluded site which is a lesion area with a catheter to restore the blood flow. In addition, the term "assistance" may imply, for example, performing intravascular image diagnosis before and after treatment to evaluate treatment effects and collect information required to determine the next treatment direction. Alternatively, the term "assistance" may imply an auxiliary operation of sustaining the treatment effects such as removing embolic debris and the like which are caused by the inflation of a balloon when a treatment catheter is used but cannot be recovered with the treatment catheter, preventing the restenosis of a blood vessel that is restored by treatment, or extending the patency period of a blood vessel.

A guiding catheter, a guiding sheath, a long sheath, or the like with a thin wall which can be introduced from one arm and into which a balloon catheter with a large outer diameter can be inserted to be able to dilate a lesion area with a large blood vessel diameter such as the iliac artery or the femoral artery is used as a first catheter. Specifically, a first guiding catheter as the first catheter preferably has an inner diameter of 2.2 mm, an outer diameter of 2.3 to 2.6 mm, and a total length of approximately 1,500 to 1,600 mm.

Examples of a first treatment catheter include a balloon catheter, a stent delivery catheter, an atherectomy catheter, and the like that have a total length of approximately 2,000 mm and dilate a stenosed site or an occluded site in a lower limb artery, and preferably include a balloon catheter with a large outer diameter which can dilate a lesion area with a large blood vessel diameter such as the iliac artery or the femoral artery, specifically, a balloon catheter in which the inflation diameter (outer diameter) of a balloon portion is from approximately 5 to 12 mm and the length of the balloon portion is from approximately 20 to 300 mm, and a stent delivery catheter that disposes a stent in which the inflation diameter (inner diameter) is 5 to 12 mm and the length of a balloon portion is from approximately 20 to 300 mm. In addition, examples of the first treatment catheter include a drug-coated balloon (DCB) catheter that carries a drug and a stent delivery catheter that disposes a drug-eluting stent (DES).

Alternatively, a blood vessel penetrating catheter or a guide wire support catheter for restoring the blood flow in an occluded site or an embolus aspiration catheter for removing emboli may be used as the first treatment catheter before the DCB or DES is used. Alternatively, an atherectomy catheter or a balloon catheter for performing vessel preparation may be used as the first treatment catheter to improve the effect of a drug.

In addition to the same catheters as those that are used as the first catheter, an angiographic catheter, a guide wire support catheter, a microcatheter, or the like may be used as a second catheter which is inserted into a blood vessel of the other arm.

In order to assist the first catheter in performing treatment, the second catheter may be used as an aspiration catheter, for example, to remove emboli caused by the inflation of the balloon catheter serving as the first treatment catheter or a cholesterol crystal or the like accumulated in plaque.

In addition to being the same catheters as those that are used as the first treatment catheter, the second treatment catheter may be an intravascular image diagnostic catheter such as an IVUS catheter that performs image diagnosis of the inner surface of the blood vessel before and after treatment, and may be inserted and used in the blood vessel.

FIG. 1 illustrates a state where a guiding catheter 10 serving as the first catheter is disposed in a blood vessel of a patient having a stenosed site (lesion area) X in the left superficial femoral artery from the right radial artery, a DCB catheter 12 serving as the first treatment catheter is disposed in a lumen of the first catheter, and a guiding catheter 10' serving as the second catheter is disposed in the left radial artery.

In a first disposition step, after an operator punctures the right radial artery of a patient (living body) with a puncture needle (not illustrated) and disposes a mini-guide wire (not illustrated) in the blood vessel, the operator inserts a sheath introducer 11 incorporating a dilator (not illustrated). Next, the operator removes the dilator and the mini-guide wire, and then introduces the guiding catheter 10, which is the first catheter incorporating a guide wire 13, through the sheath introducer 11.

The radial artery (radial) accessed by the operator may be, in addition to the conventional radial artery in the vicinity of the wrist (i.e., the traditional access point of the radial artery in the vicinity of the patient's wrist as known in the art), a distal radial artery which is closer to a peripheral side or a radial artery in the snuffbox. Here, the radial artery in the snuffbox is a radial artery in a site that is positioned on the peripheral side of the radial artery between the extensor pollicis brevis and the extensor hallucis longus, and is hereinafter referred to as s-RA. The distal radial artery is a dorsal carpal branch of the radial artery and a radial artery that is positioned between the extensor hallucis longus and the extensor carpi radialis longus, and is hereinafter referred to as d-RA.

Subsequently, the operator inserts the guide wire 13 into a left common iliac artery side to dispose the guide wire 13 beyond the stenosed site X in the left superficial femoral artery through the left common femoral artery from the left external iliac artery. Subsequently, a distal portion 10a of the guiding catheter 10 is advanced along the guide wire 13 to a location in front of the lesion area, specifically, to a location beyond bifurcated branches of the left superficial femoral artery and the left deep femoral artery, and the guiding catheter 10 is disposed in the lower limb artery.

Next, in an introduction step, the operator introduces the guiding catheter 10', which is the second catheter, into the conventional radial artery of the left arm (i.e., the traditional access point of the radial artery in the vicinity of the patient's wrist as known in the art). A distal portion 10a' of the second guiding catheter 10' is disposed at a position where the second guiding catheter 10' can assist the treatment without disrupting the first catheter and the first treatment catheter from performing the treatment. In FIG. 1, the distal portion 10a' is disposed in front of the stenosed site X.

Furthermore, in a second disposition step, the operator disposes a DCB 12a of the drug-coated balloon (DCB) catheter 12, which is the first treatment catheter, at the stenosed site X. Specifically, in order to dilate the stenosed site X, a rapid exchange (RX) type of the DCB catheter 12 is advanced to a stenosed site X side along the guide wire 13, and the DCB 12a which is a treatment portion is disposed from a proximal end to a terminus end of the stenosed site X.

Next, in a treatment step, the operator attaches an inflator or inflation device (not illustrated) to the DCB catheter 12 and injects a liquid thereinto to inflate the DCB 12a; and thereby, the stenosed site X is dilated. When the DCB 12a is inflated by the inflator (not illustrated), which is attached to a catheter hub, to dilate the stenosed site, the plaque breaks up and a cholesterol crystal 141 is released into the blood vessel.

In a step of assisting the treatment of the stenosed site X with the second catheter, the operator aspirates and removes the cholesterol crystal 141, which might otherwise occlude peripheral blood vessels to cause a cholesterol embolism, with the second catheter to reduce complications and assist the treatment.

Furthermore, the operator operates the inflator to reduce the pressure supplied by the inflator and deflate the DCB 12a after the stenosed site is coated with the drug; and thereby, the blood flow is restored. Since there is a possibility that the cholesterol crystal 141 or a drug 140 incapable of penetrating into the blood vessel wall flows toward the peripheral side or in the peripheral direction to possibly cause an embolism or the like due to the restored blood flow, the cholesterol crystal 141 or the drug 140 may be aspirated and removed in the same manner, that is by use of the second catheter.

Specifically, in the treatment assistance step, in this embodiment, in FIG. 1, the operator attaches a Y-connector (not illustrated) to a proximal end opening portion of a hub of the second guiding catheter 10', and attaches an aspirator to a side port. For example, a syringe (not illustrated) may be used as the aspirator. The operator operates the Y-connector and the syringe to adjust the pressure in a lumen of the second guiding catheter 10' so that the lumen of the second guiding catheter 10' is under a negative pressure. An aspiration force is generated by the negative pressure; and thereby, it is possible to assist the treatment by taking away, out of the body, at least fat-soluble compounds such as cholesterol crystals, which are formed from emboli or plaque and positioned between an occluded proximal side of the DCB 12a and an opening portion of the distal portion 10a of the first guiding catheter, in other words, between the DCB 12a and a heart side (upstream) of the stenosed site X.

When the DCB catheter 12 cannot enter the stenosed site X, the operator may use an atherectomy catheter as another treatment catheter in advance to open a hole in the stenosed site X, and the operator may then cause the DCB catheter 12 to enter the stenosed site X. In this case, the operator may exchange the DCB catheter 12 with the atherectomy catheter to insert the atherectomy catheter into the same first guiding catheter 10 from the radial artery of the same arm, or may perform the treatment by disposing the atherectomy catheter in the stenosed site X through the second guiding catheter 10' inserted into the other arm in a state where the DCB catheter is indwelled in the first guiding catheter 10 and inserted into the body.

As an assistance to the treatment, an IVUS catheter may be disposed in the guiding catheter 10' all the time to confirm (visualize) the inner surface of the blood vessel before and after dilation. Particularly, when the second catheter is not a treatment catheter such as a balloon catheter but is only an IVUS catheter and inserted into the blood vessel, a second guiding catheter having a smaller outer diameter than that of the first guiding catheter may be used. When the second catheter with a small outer diameter is used, an access from the s-RA or d-RA is low invasive, which is preferable.

Another Embodiment

When the stenosed site X is positioned in one artery in the vicinity of a bifurcated portion, the operator dilates the stenosed site X with a first balloon catheter inserted into the first catheter. In this case, in order to prevent the inflation of the balloon from causing the occlusion of another artery, the operator may simultaneously dilate a main branch blood vessel and a bifurcated branch blood vessel in the lesion area with a second balloon catheter inserted into the second catheter that is introduced from the other arm. Therefore, it is possible to assist the treatment such that other blood vessels are not occluded.

In addition, when the first catheter is disposed from the artery of the arm to the lower limb artery, the first catheter may move in the aorta to abrade the inner wall of the aorta. Emboli which are formed from the plaque on the inner wall of the aorta, or calcified lesions which are separated due to the abrasion may scatter to the superior mesenteric artery to cause SMAO. In a high emergency case such as the patient reaching intestinal necrosis, the operator removes emboli in the superior mesenteric artery in a state where the first catheter and the first treatment catheter remain disposed in the lesion area. For example, the operator may aspirate the emboli using the second guiding catheter which is the second catheter, or may insert a balloon catheter or a stent delivery catheter which is the second treatment catheter into the second guiding catheter to dilate the blood vessel and treat the SMAO.

In addition, the roles may be changed between the first catheter and the second catheter, the lesion area may be treated with the second catheter and the treatment may be assisted with the first catheter, or the roles may be changed therebetween in the middle of treatment.

Since two catheters are inserted from both arms into a lesion area in a lower limb artery which takes time to treat, the time required to exchange a treatment catheter or a diagnostic catheter is reduced, and there is no interruption in the treatment of the lesion area even when acute embolism occurs in a site other than the lesion area; and thereby, it is possible to complete the entire treatment of a patient in a short period of time. Therefore, it is possible to reduce labor costs, which contributes to the medical economic efficiency.

The detailed description above describes embodiments of a treatment method representing examples of the inventive treatment method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A treatment method for treating a patient having a lesion area in a lower limb artery of a body of the patient, the patient having a first arm and a second arm, the treatment method comprising:
   introducing a first catheter into an artery of the first arm of the patient;
   advancing the first catheter, which has been introduced into the artery of the first arm of the patient, in the body of the patient to approach the lesion area from above the lesion area and to position a distal portion of the first catheter adjacent the lesion area in the lower limb artery and upstream of the lesion area;
   introducing a second catheter into an artery of the second arm of the patient;
   advancing the second catheter, which has been introduced into the artery of the second arm of the patient, in the body of the patient to approach the lesion area from above the lesion area and to position a distal portion of the second catheter adjacent the lesion area in the lower limb artery and upstream of the lesion area;
   introducing a balloon catheter into a lumen in the first catheter or into a lumen in the second catheter while the distal portion of the first catheter and the distal portion of the second catheter are upstream of the lesion area and advancing the balloon catheter along the lumen to position a distal end portion of the balloon catheter outside and distally beyond the lumen;
   treating the lesion area by enlarging a hole in the lesion area through expansion of a balloon of the balloon catheter that is positioned outside the lumen to bring the balloon into contact with the lesion area, the treating of the lesion area occurring while the distal portion of the first catheter and the distal portion of the second catheter are upstream of the lesion area, the treating of the lesion area producing emboli or cholesterol crystals;
   the treating of the lesion area being carried out after the advancing of the first catheter to the position adjacent the lesion area and after the advancing of the second catheter to the position adjacent the lesion area; and
   creating suction in the lumen of the second catheter while the distal portion of the first catheter and the distal portion of the second catheter are positioned in side-by-side relation to one another and are both facing in a common direction toward the lesion area to draw into the lumen of the second catheter the emboli or cholesterol crystals that are between the balloon that is in contact with the lesion area and an opening at a distal end of the second catheter.

2. The treatment method according to claim 1, wherein the balloon catheter is a first treatment catheter that is introduced into the lumen in the first catheter, and further comprising introducing a second treatment catheter into the lumen in the second catheter and advancing the second treatment catheter along the lumen of the second catheter to position a distal end portion of the second treatment catheter outside and distally beyond the lumen in the second catheter.

3. The treatment method according to claim 1, further comprising introducing a guidewire into the artery of the second arm of the patient before introducing the second catheter into the artery of the second arm of the patient, and advancing the guidewire to adjacent the lesion area, the advancing of the second catheter in the body of the patient comprising advancing the second catheter along the guide wire.

4. The treatment method according to claim 1, wherein at least one of the first artery and the second artery is a radial artery.

5. The treatment method according to claim 1, wherein at least one of the first artery and the second artery is a distal radial artery or a radial artery in a snuffbox.

6. The treatment method according to claim 1, wherein the lesion area in the lower limb artery is a stenosed site in a superficial femoral artery.

7. The treatment method according to claim 1, further comprising inserting a guide wire into the first artery and advancing the guide wire through a left common iliac artery of the patient to a superficial femoral artery of the patient, the advancing of the first catheter in the body comprising advancing the first catheter along the guide wire.

8. The treatment method according to claim 1, wherein the lumen into which the balloon catheter is introduced is different from the lumen in which the suction is created.

9. The treatment method according to claim 1, wherein the introducing of the balloon catheter includes introducing the balloon catheter into the lumen in the first catheter, the creating of the suction in the lumen of the second catheter occurring after the second catheter is used to treat a lesion different from the lesion area.

10. A treatment method for a patient having a lesion area in a lower limb artery, the patient having one arm and an other arm, the method comprising:
    introducing a first catheter into an artery of the one arm of the patient to position a distal portion of the first catheter upstream of the lesion area in the lower limb artery;
    introducing a second catheter into an artery of the other arm of the patient, the second catheter possessing a distal portion;
    disposing a balloon catheter adjacent the lesion area through the first catheter;
    treating the lesion area with the balloon catheter while the distal portion of the first catheter is upstream of the lesion area, the treating of the lesion area with the balloon catheter comprising expanding a balloon of the balloon catheter so that the balloon expands into contact with the lesion area;
    assisting the treating of the lesion area with the second catheter and with a treatment catheter that is inserted into the second catheter, the assisting of the treating of the lesion area with the second catheter occurring while the distal portion of the second catheter is upstream of the lesion area, the assisting of the treating of the lesion area with the treatment catheter inserted into the second catheter occurring after the treatment catheter has been used to treat a lesion different from the lesion area; and
    the assisting of the treating of the lesion area with the second catheter comprising creating suction in the second catheter while the distal portion of the first catheter and the distal portion of the second catheter are positioned in side-by-side relation to one another and are both facing in a common direction toward the lesion area, the creating of the suction in the second catheter occurring while the balloon is in contact with the lesion area, the suction being performed to draw into the second catheter emboli or cholesterol crystals that are produced by the balloon contacting the lesion area and that are located between the balloon in contact with the lesion area and an open distal end of the second catheter.

11. The treatment method according to claim 10, wherein at least one of the artery of the one arm and the artery of the other arm is a radial artery.

12. The treatment method according to claim 11, wherein at least one of the artery of the one arm and the artery of the other arm is a distal radial artery or a radial artery in a snuffbox.

13. The treatment method according to claim 10, wherein at least one of the artery of the one arm and the artery of the other arm is a distal radial artery or a radial artery in a snuffbox.

14. The treatment method according to claim 10, wherein the lesion area in the lower limb artery is a stenosed site in a superficial femoral artery.

15. The treatment method according to claim 10, further comprising inserting a guide wire into the artery of the one arm of the patient and advancing the guide wire through a left common iliac artery of the patient to a superficial femoral artery of the patient, and the introducing of the first catheter into the artery of the one arm of the patient to position the distal portion of the first catheter at least in front of the lesion area in the lower limb artery comprises advancing the first catheter along the guide wire.

16. A treatment method for a patient having a lesion area in a lower limb artery, the patient having one arm and an other arm, the method comprising:
   introducing a first catheter into an artery of the one arm of the patient and advancing the first catheter to approach the lesion area from above the lesion area and to position a distal portion of the first catheter upstream of the lesion area in the lower limb artery;
   introducing a second catheter into an artery of the other arm of the patient and advancing the second catheter to approach the lesion area from above the lesion area;
   disposing a balloon catheter adjacent the lesion area through the first catheter;
   treating the lesion area with the balloon catheter while the distal portion of the first catheter is upstream of the lesion area, the treating of the lesion area with the balloon catheter comprising expanding a balloon of the balloon catheter so that the balloon expands into contact with the lesion area;
   assisting the treating of the lesion area: i) with the second catheter while the distal portion of the second catheter is upstream of the lesion area; and ii) with a treatment catheter that is inserted into the second catheter while the distal portion of the second catheter is upstream of the lesion area; and
   the assisting of the treating of the lesion area with the second catheter comprising creating suction in the second catheter and/or the treatment catheter while the distal portion of the first catheter and the distal portion of the second catheter are positioned in side-by-side relation to one another and are both facing in a common direction toward the lesion area, the creating of the suction in the second catheter and/or the treatment catheter occurring while the balloon is in contact with the lesion area, the suction being performed to draw into the second catheter and/or the treatment catheter emboli or cholesterol crystals that are produced by the balloon contacting the lesion area and that are located between the balloon in contact with the lesion area and an open distal end of the second catheter.

17. The treatment method according to claim 16, further comprising using the second catheter and/or the second treatment catheter to perform treatment of a lesion different from the lesion area before the assisting of the treating of the lesion area with the second catheter and/or with a second treatment catheter.

* * * * *